United States Patent
Muhs et al.

(10) Patent No.: US 7,231,128 B2
(45) Date of Patent: Jun. 12, 2007

(54) HYBRID SOLAR LIGHTING SYSTEMS AND COMPONENTS

(75) Inventors: Jeffrey D. Muhs, Lenoir City, TN (US); Dennis D. Earl, Knoxville, TN (US); David L. Beshears, Knoxville, TN (US); Lonnie C. Maxey, Powell, TN (US); John K. Jordan, Oak Ridge, TN (US); Randall F. Lind, Lenoir City, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 794 days.

(21) Appl. No.: 10/633,027

(22) Filed: Aug. 1, 2003

(65) Prior Publication Data

US 2004/0118447 A1 Jun. 24, 2004

Related U.S. Application Data

(63) Continuation-in-part of application No. 09/953,848, filed on Sep. 18, 2001, now Pat. No. 6,603,069.

(51) Int. Cl.
*G02B 6/00* (2006.01)
*H01L 31/042* (2006.01)
*C12M 1/00* (2006.01)
*F24J 2/10* (2006.01)

(52) U.S. Cl. ............ 385/900; 385/147; 136/246; 136/253; 136/291; 136/248; 435/292.1; 126/683; 126/685; 126/690; 60/641.8

(58) Field of Classification Search ............ 385/88, 385/89, 92, 94, 900, 901, 147; 136/246, 136/253, 291, 248; 250/227.11; 126/683, 126/685, 690, 683.685; 60/641.8; 435/292.1
See application file for complete search history.

(56) References Cited

U.S. PATENT DOCUMENTS

| | | | | |
|---|---|---|---|---|
| 3,427,093 | A | * | 2/1969 | Maples et al. ............ 359/236 |
| 4,029,519 | A | * | 6/1977 | Schertz et al. ............ 136/246 |
| 4,297,000 | A | | 10/1981 | Fries .................... 385/115 X |
| 4,328,389 | A | | 5/1982 | Stern et al. .............. 136/246 |
| 4,525,031 | A | | 6/1985 | Mori ..................... 350/265 |
| 4,539,625 | A | | 9/1985 | Bornstein et al. .......... 362/32 |
| 4,626,065 | A | | 12/1986 | Mori ................... 385/115 X |
| 4,700,013 | A | | 10/1987 | Soule .................... 136/248 |
| 4,970,166 | A | | 11/1990 | Meri .................... 435/313 |
| 5,371,660 | A | | 12/1994 | Levens ................... 362/145 |
| 5,575,860 | A | | 11/1996 | Cherney .................. 136/245 |
| 5,614,378 | A | | 3/1997 | Yang et al. .............. 435/41 |
| 5,658,448 | A | | 8/1997 | Lasich ................... 205/626 |
| 5,716,442 | A | | 2/1998 | Fertig .................... 136/246 |
| 6,128,135 | A | | 10/2000 | Stiles et al. ............. 359/597 |

(Continued)

FOREIGN PATENT DOCUMENTS

DE 19705046 A1 2/1998 ............ 385/147 X (Continued)

*Primary Examiner*—Brian M. Healy
(74) *Attorney, Agent, or Firm*—Kirk A. Wilson

(57) ABSTRACT

A hybrid solar lighting system and components having at least one hybrid solar concentrator, at least one fiber receiver, at least one hybrid luminaire, and a light distribution system operably connected to each hybrid solar concentrator and each hybrid luminaire. A controller operates each component.

7 Claims, 11 Drawing Sheets

U.S. PATENT DOCUMENTS

| | | | |
|---|---|---|---|
| 6,188,177 B1 * | 2/2001 | Adamson et al. | 315/149 |
| 6,603,069 B1 * | 8/2003 | Muhs et al. | 136/246 |
| 2004/0118447 A1 * | 6/2004 | Muhs et al. | 136/246 |
| 2004/0187908 A1 * | 9/2004 | Muhs et al. | 136/246 |

FOREIGN PATENT DOCUMENTS

| | | | | |
|---|---|---|---|---|
| EP | 0019016 | 11/1980 | ............ | 385/147 X |
| EP | 0922914 A2 | 6/1999 | ............ | 385/147 X |
| GB | 2 029 8831 A | 3/1980 | ............ | 385/147 X |
| JP | 57-181689 | 11/1982 | ............ | 385/147 X |
| JP | 61-139382 | 6/1986 | ............ | 385/147 X |
| JP | 4-84883 | 3/1992 | ............ | 385/147 X |
| JP | 5-64577 | 3/1993 | ............ | 385/147 X |
| JP | 8-200839 | 8/1996 | ............ | 385/147 X |
| JP | 8-329712 | 12/1996 | ............ | 385/147 X |

* cited by examiner

HYBRID SOLAR LIGHTING SYSTEMS AND COMPONENTS

CROSS REFERENCE TO RELATED APPLICATIONS

This application is a continuation-in-part of U.S. patent application Ser. No. 09/953,848 filed on Sep. 18, 2001, to be issued as U.S. Pat. No. 6,603,069 on Aug. 5, 2003, and is herein incorporated by reference in its entirety.

STATEMENT REGARDING FEDERAL SPONSORSHIP

This invention was made with Government support under contract no. DE-AC05-00OR22725 to UT-Battelle, LLC, awarded by the United States Department of Energy. The Government has certain rights in the invention.

FIELD OF THE INVENTION

This invention relates to the field of solar energy systems and more specifically to hybrid solar lighting systems and components having hybrid solar concentrator collector(s) for capturing incident solar radiation and using portions of the solar spectrum for direct lighting. Direct lighting is distributed to hybrid luminaire fixtures.

BACKGROUND OF THE INVENTION

Throughout the 1900s, use of the sun as a source of energy has evolved considerably. Early in the century, the sun was the primary source of interior light for buildings during the day. Eventually, however, the cost, convenience, and performance of electric lamps improved and the sun was displaced as our primary method of lighting building interiors. This, in turn, revolutionized the way we design buildings, particularly commercial buildings, making them minimally dependent on natural daylight. As a result, lighting now represents the single largest consumer of electricity in commercial buildings.

During and after the oil embargo of the 1970s, renewed interest in using solar energy emerged with advancements in daylighting systems, hot water heaters, photovoltaics, etc. Today, daylighting approaches are designed to overcome earlier shortcomings related to glare, spatial and temporal variability, difficulty of spatial control and excessive illuminance. In doing so, however, they waste a significant portion of the visible light that is available by shading, attenuating, and or diffusing the dominant portion of daylight, i.e., direct sunlight which represents over 80% of the light reaching the earth on a typical day. Further, they do not use the remaining half of energy resident in the solar spectrum (mainly infrared radiation between 0.7 and 1.8 µm), add to building heat gain, require significant architectural modifications, and are not easily reconfigured. Previous attempts to use sunlight directly for interior lighting via fresnel lens collectors, reflective light-pipes, and fiber-optic bundles have been plagued by significant losses in the collection and distribution system, ineffective use of nonvisible solar radiation, and a lack of integration with collocated electric lighting systems required to supplement solar lighting on cloudy days and at night.

BRIEF SUMMARY OF THE INVENTION

This invention improves the total end-use power displacement efficiency of solar energy by integrating solar technologies into multi-use hybrid systems that better utilize the entire solar energy spectrum. As illustrated in FIG. 1, a primary mirror 30 concentrates the entire solar spectrum of incoming sunlight onto a secondary mirror 31 where the sunlight is reflected into a fiber receiver 32 for filtering and distribution to the fiberoptic lighting network.

This hybrid solar lighting (HSL) solar energy system is a unique alternative to solar energy use in buildings. It uses solar energy from a dynamic, systems-level perspective, integrates multiple interdependent technologies, and makes better use of the entire solar energy spectrum on a real-time basis.

The HSL system uses a hybrid solar concentrator that efficiently collects, separates, and distributes the visible portion of sunlight. The optical and mechanical properties of improved large-core polymer optical fiber light distribution system more efficiently deliver large quantities of visible sunlight into buildings. Once delivered, the visible sunlight is used much more effectively than previously to illuminate building interiors using new hybrid luminaires.

This invention redirects and more efficiently uses portions of the solar energy spectrum originating from a common two-axis, tracking solar concentrator in real-time using electro-optic and or opto-mechanical devices. Analytical/experimental models and intelligent control strategies enhance the use of hybrid solar lighting systems in many applications including commercial buildings, display lighting, billboards, pools, spas, street lights, ships, and photobioreactors using either sunlight sources or man-made light sources.

DETAILED DESCRIPTION

In the hybrid solar lighting (HSL) system, the luminous efficacy of filtered sunlight is more than double its only competition (electric lamps). Therein lies the primary motivation for using filtered sunlight for lighting purposes in buildings.

Figure 1:
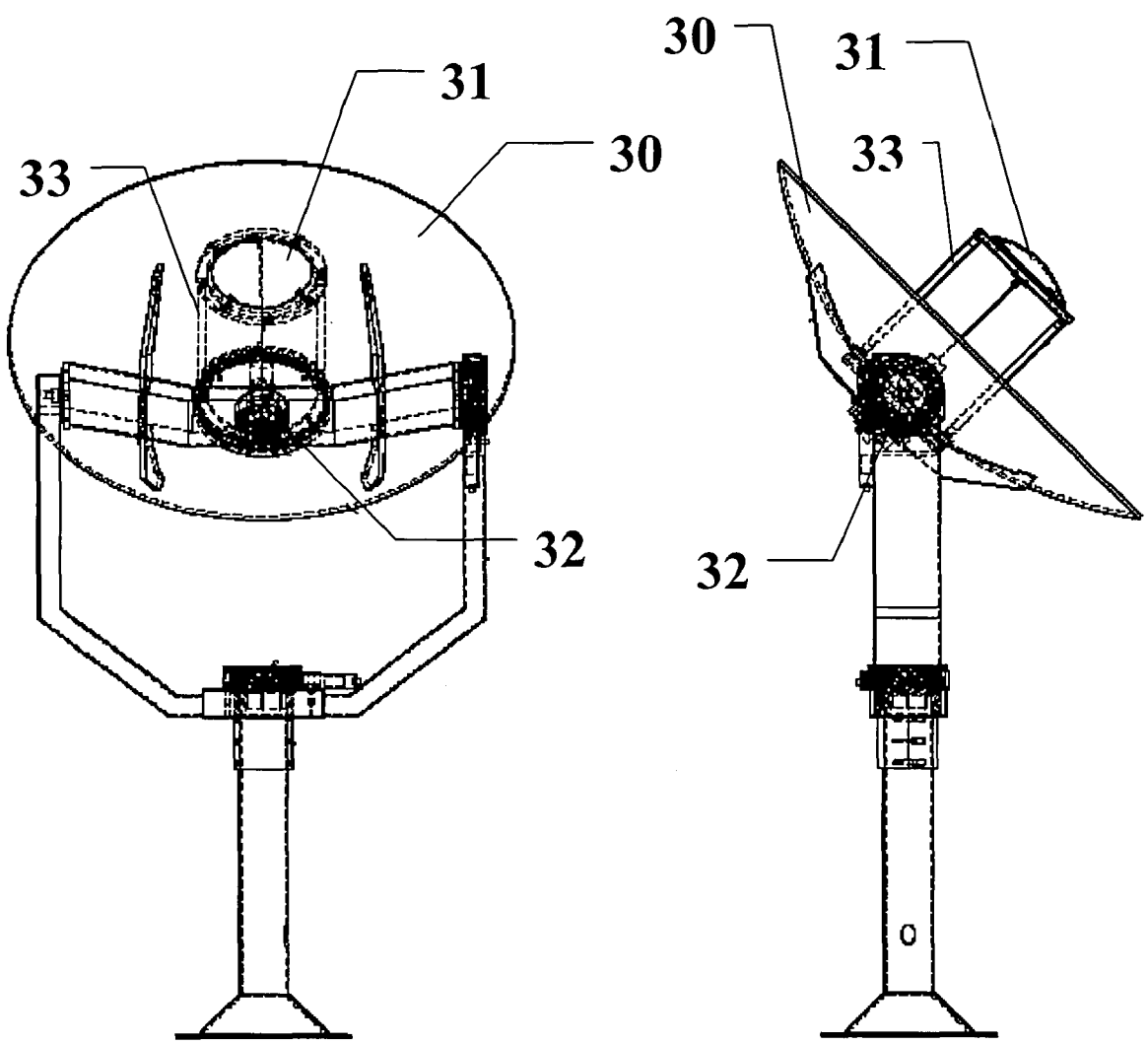
FIG. 1 shows the major components of the hybrid solar concentrator.
Figure 2:
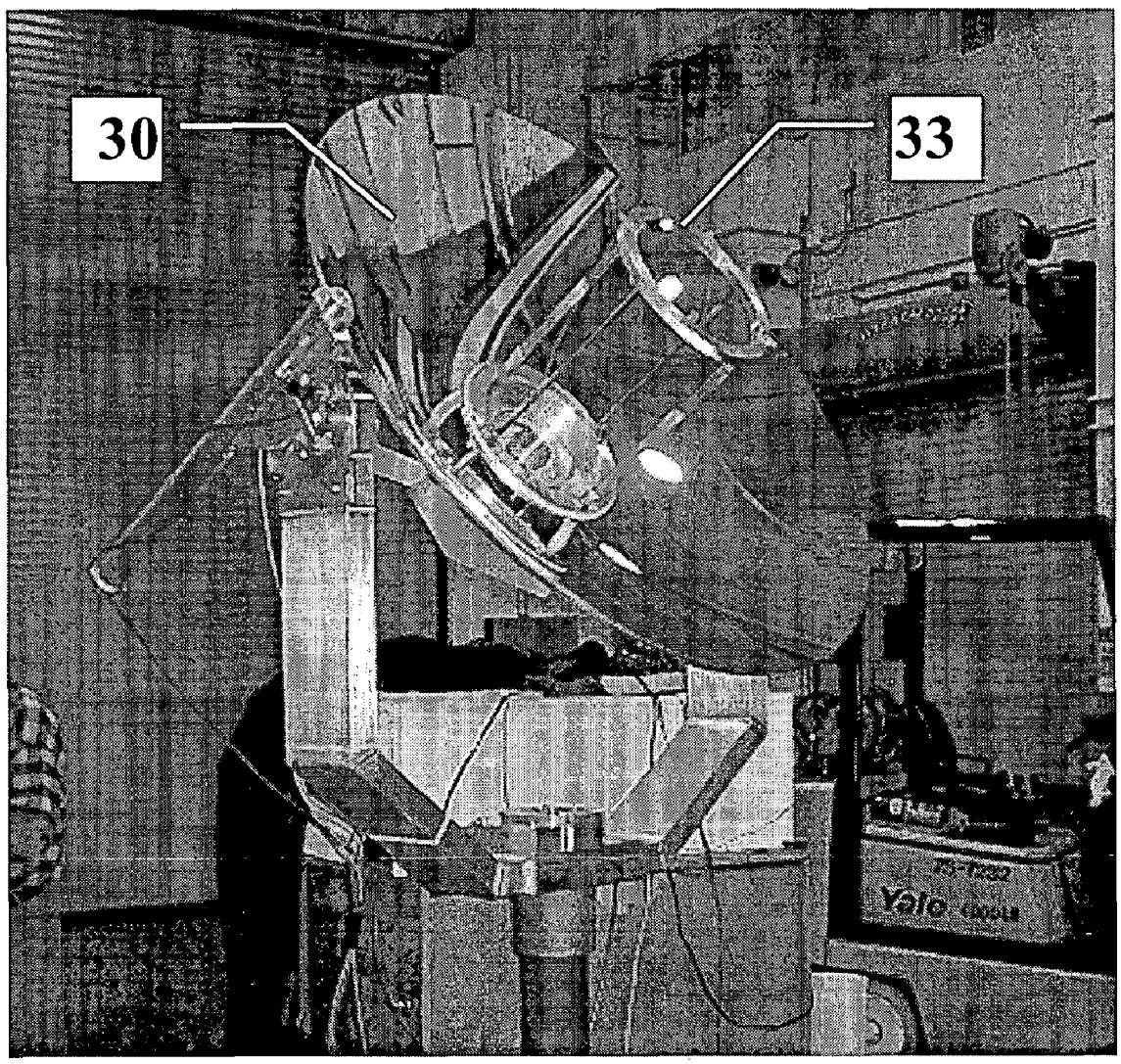
FIG. 2 is a front view photograph of the hybrid solar collector.
Figure 3:
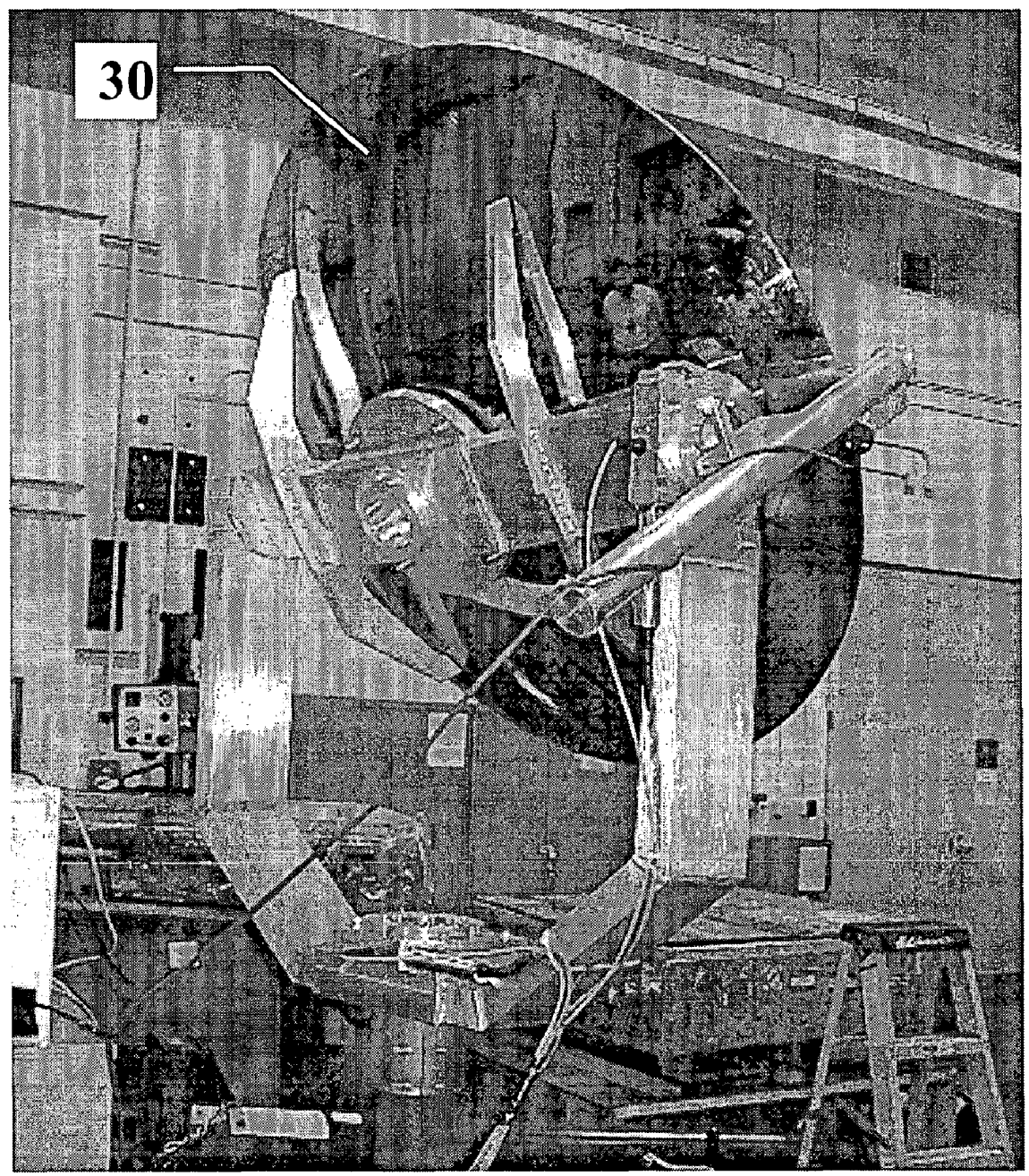
FIG. 3 is a rear view photograph of the hybrid solar collector.
Figure 4:
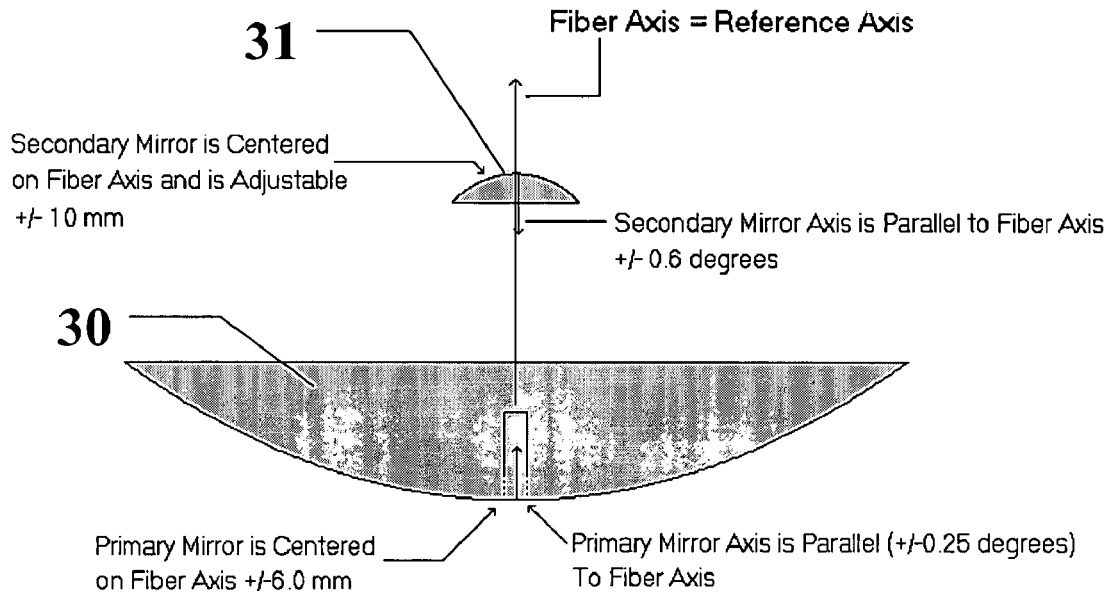
FIG. 4 shows preferred optical specifications for the primary and secondary mirror.
Figure 4:
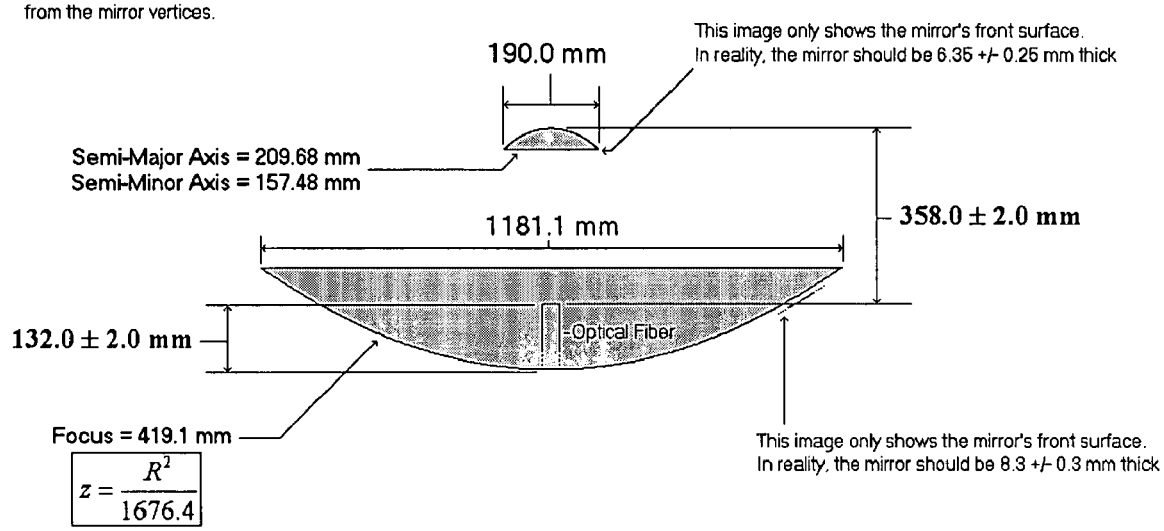
Figure 5:
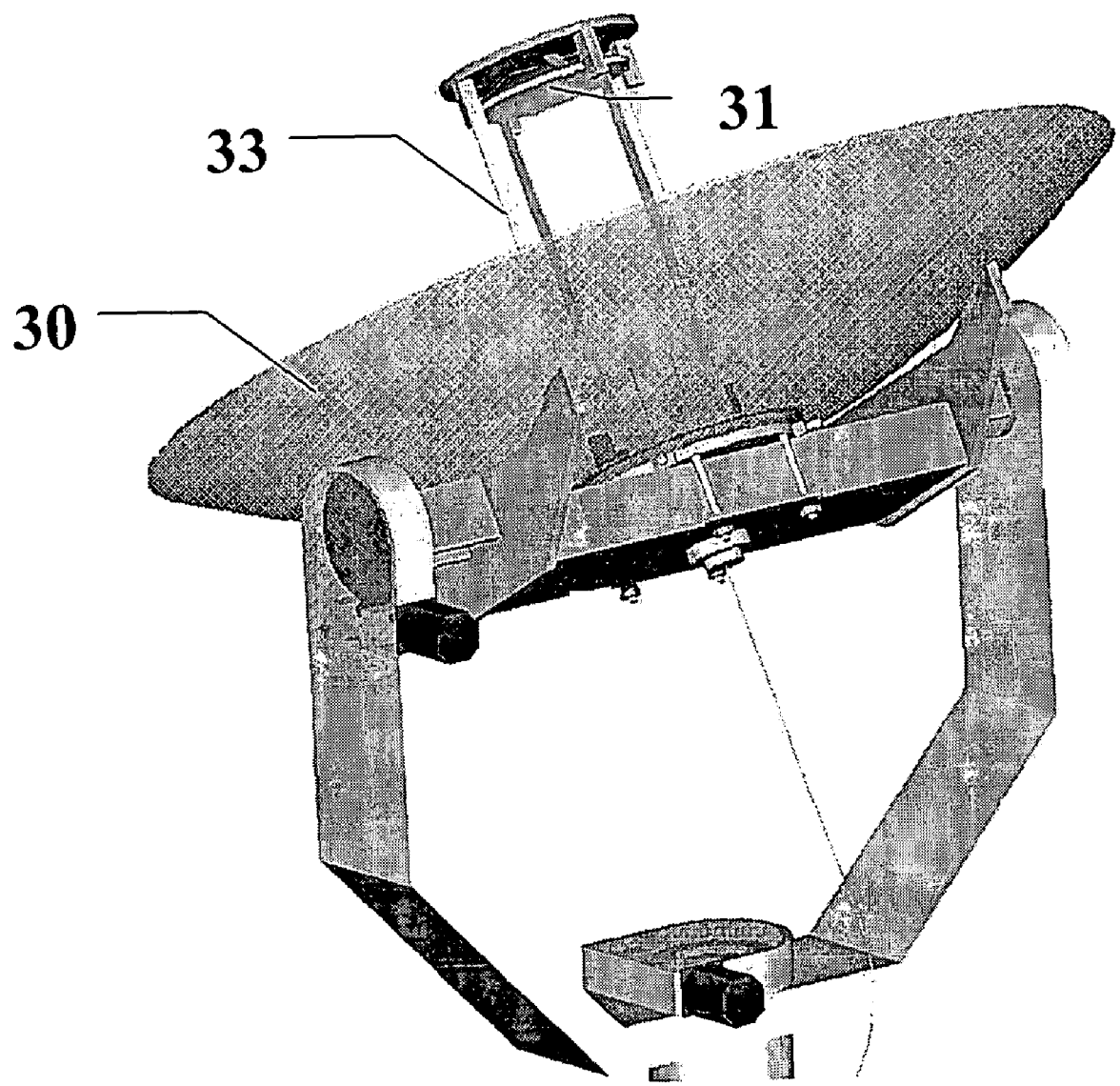
FIG. 5 is a rear view rendering of the hybrid solar collector.

FIG. 1 illustrates a preferred embodiment of the hybrid solar concentrator where a primary mirror 30 concentrates the entire solar spectrum of incoming sunlight onto a secondary mirror 31 where the sunlight is reflected into a fiber receiver 32 for filtering and distribution to the fiberoptic lighting network. FIG. 2 is a front view photograph showing the primary mirror 30 and the secondary mirror mount 33. The secondary mirror mount 33 blocks less than 5% of the sunlight reflected from the primary mirror 30. Structural features of the secondary mount 33 enable the mount to flex while maintaining the preferred optical specifications in FIG. 4. The flexure in the mount 33 relieves stress points where the mount 33 attaches to the primary mirror 30. FIG. 5 is a rendering showing the secondary mirror 31 mounted to the secondary mount 33.

Figure 6:
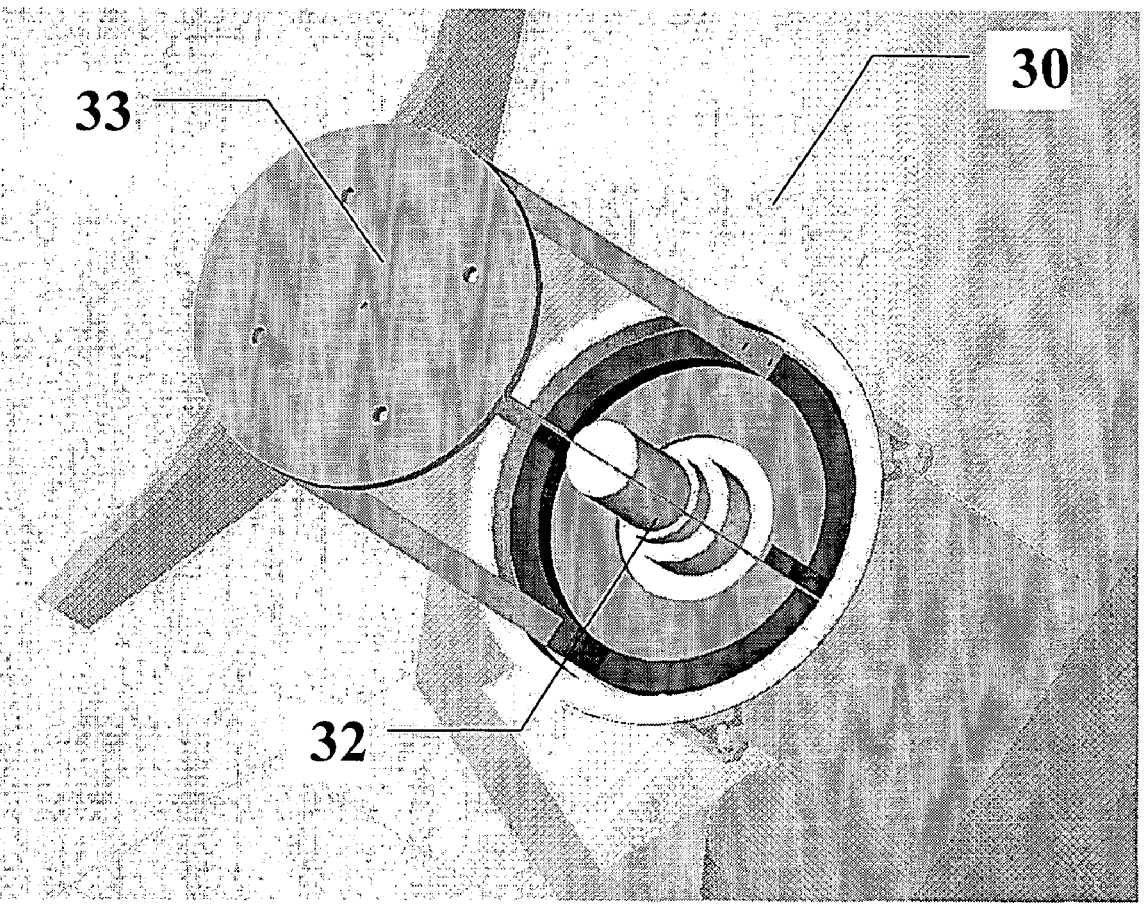
FIG. 6 is a rendering of the fiber receiver mounted in the concentrator.
Figure 7:
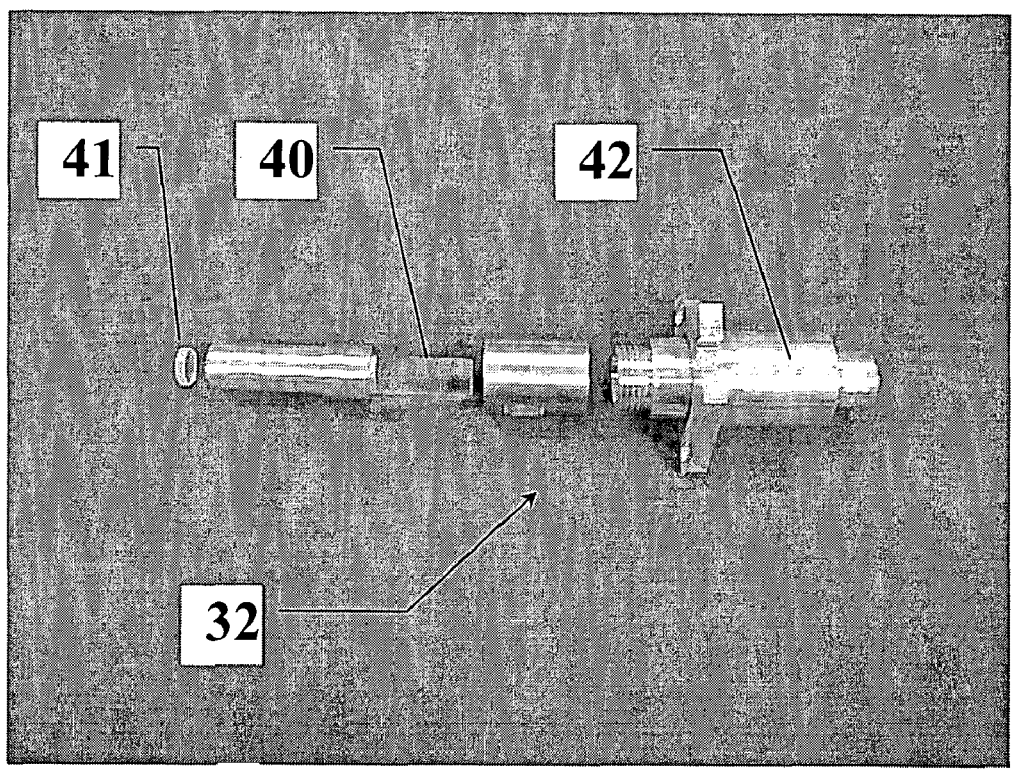
FIG. 7 is two photographs, assembled and unassembled, of the fiber receiver.
Figure 7:
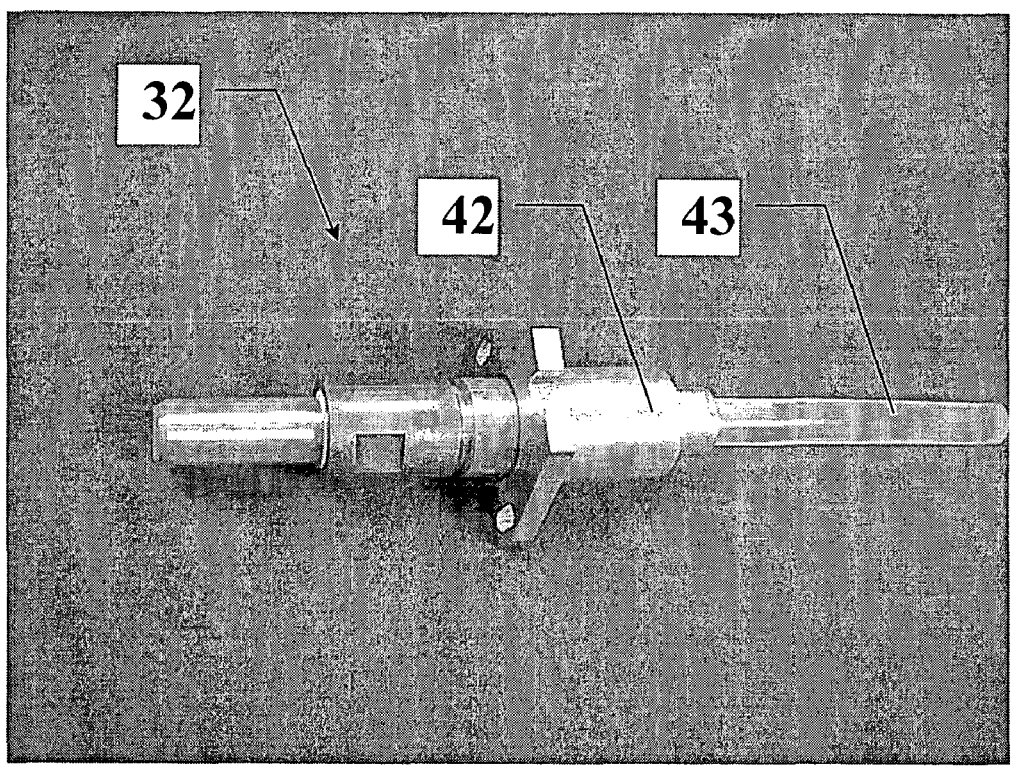

FIG. 6 shows the fiber receiver 32 mounted in the center core of the primary mirror 30. FIG. 7 shows the fiber receiver 32 components including a quartz rod 40 to act as heat dissipation means and filter 41 to reject remaining IR energy. Fiber 43 is forcibly bonded to quartz rod 40 inside the receiver housing 42 to minimize fresnel losses and associated thermal loading. Light emerging from the rod 40 into the fiber 43 is uniformly distributed so as to maximize the amount of light that can be injected into the polymer fibers. Also the focal spot on the quartz rod 40 can be smaller than its diameter so as to reduce the tracking accuracy needs of the system.

For building applications, the most significant loss factor in the light collection and distribution system is the end-to-end attenuation in large-core optical fibers. This invention more efficiently and cost-effectively transports sunlight through new polymer-based large-core optical fibers rather than glass fiber optic bundles. A new "hybrid" luminaire, illustrated spatially distributes both fiberoptic-delivered sunlight and electric light in a general lighting application and controlling the relative intensity of each based on sunlight availability using photosensors and dimmable electronic ballasts. Thus, natural light is collected at a central location and distributed to multiple luminaires.

One embodiment of the hybrid luminaire comprised a cylindrical diffusing rod having a 2.54 cm diameter, 1.0 m long, optically clear cylinder with a polished lower hemisphere and a diffuse upper hemisphere. Light launched from a butt-coupled optical fiber, scatters from the diffuse upper surface of the cylinder and escapes through the polished lower surface of the cylinder. To improve efficiency, upward-scattered light is redirected back toward the lower hemisphere of the diffusing rod with a silver-coating on the upper hemisphere.

Three diffusing rods, each placed mid-way and slightly above adjacent fluorescent lamps in a 4-tube PARAMAX Parabolic Troffer with 24-cell louvre baffle, were expected to produce a spatial intensity distribution which closely matched that of the four fluorescent tubes. However, initial modeling of the diffusing rod indicated that the intensity of the scattered light was too highly concentrated toward one end of the rod, creating uneven illumination. In addition, a large portion of the light entering the diffusing rod at small angles was not being scattered at all and, instead, was merely being reflected from the planar end of the diffusing rod back into the butt-coupled optical fiber. To overcome these deficiencies, a silver-coated concave mirror surface at the end of the rod was added to the diffusing rod model. This concave end-mirror strongly diverged low-angle incident light, hence improving the optical efficiency of the diffusing rod while also improving the overall uniformity of the scattered light. To further improve the uniformity of the scattered light, a 40 cm strip along the center of the diffusing rod's top hemisphere was modeled with a larger scattering fraction than the outer ends to increase the amount of scattered light emitted from the center of the diffusing rod.

Simulations of the spatial intensity distribution resulting from the fluorescent lamps and/or the diffusing rods revealed only minor differences between the two distributions, and only minor deviation from the fixture's original spatial intensity distribution. However, due to obstruction and scattering losses associated with the inclusion of the three diffusing rods, the optical efficiency of the fixture was decreased from 64% to 53%. The diffusing rod itself was estimated to be only 50% efficient at converting a fiber optic end-emitted source into a cylindrical source. This efficiency was strongly dependent upon the intensity profile of the fiber optic end-emitted light and the combination of scattering values used along the top surface of the diffusing rod.

The cylindrical diffusing rod was a 2.54 cm diameter, 1 m long, cast acrylic rod, with high optical clarity and optically smooth outer surface. The rod was diamond-machined on one end to create a concave surface with a radius of curvature of 4.0 cm, and polished on the other end to create a planar optical surface suitable for butt-coupling to a large-core optical fiber. The top hemisphere of the rod was sandblasted to produce a uniform scattering surface and both the top hemisphere and concave end-mirror were coated with aluminum. Due to construction limitations, the top surface did not exhibit a variable surface scatter as originally modeled.

Preliminary testing of the cylindrical diffusing rod revealed a discrepancy between the desired modeled surface scatter and the actual surface scatter created by the sandblasting technique. Because optical scattering is often difficult to accurately premodel in software, the result was not entirely unexpected. The actual surface scatter created by the sandblasting technique was much larger than modeled and created a diffusing rod with an uneven illumination. However, now given the correlation between the modeled scattering values and the actual scattering values, it is possible to re-simulate and re-design the cylindrical diffusing rod to emit a more uniform intensity distribution. Additional factors related to optical efficiency and construction costs are currently being evaluated. A luminaire design was sought that would provide a simple means of seamlessly combining the light from the fluorescent and fiber optic sources.

Figure 10:
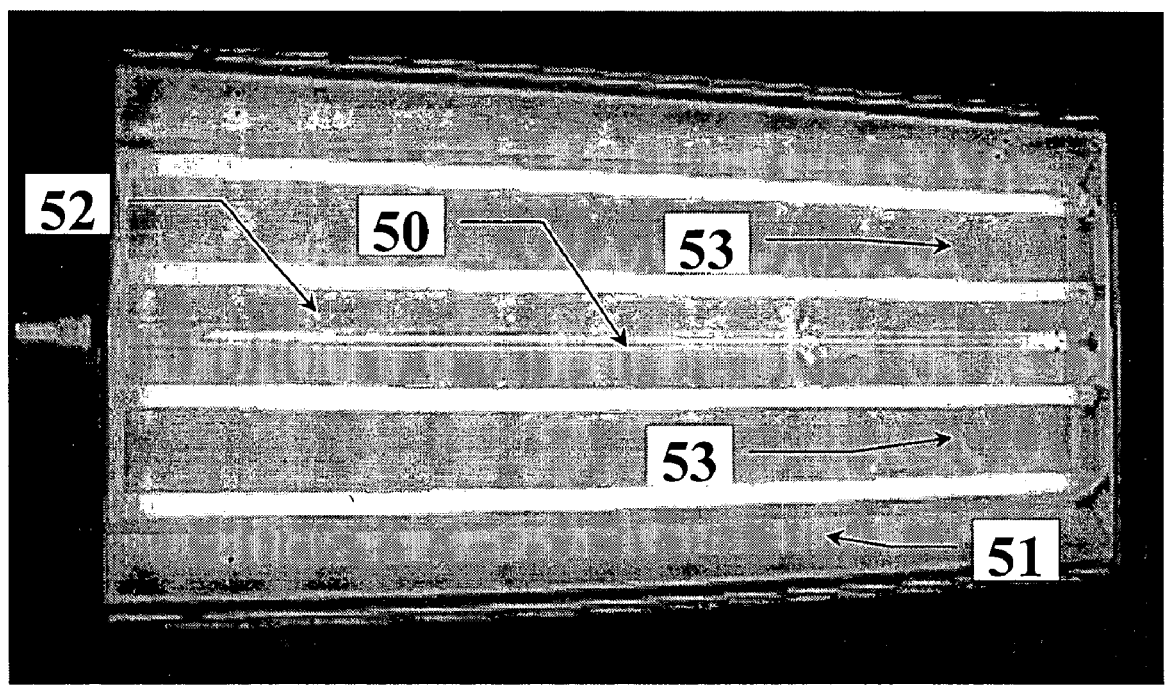
FIG. 10 is a photograph of a hybrid luminaire.
Figure 11:
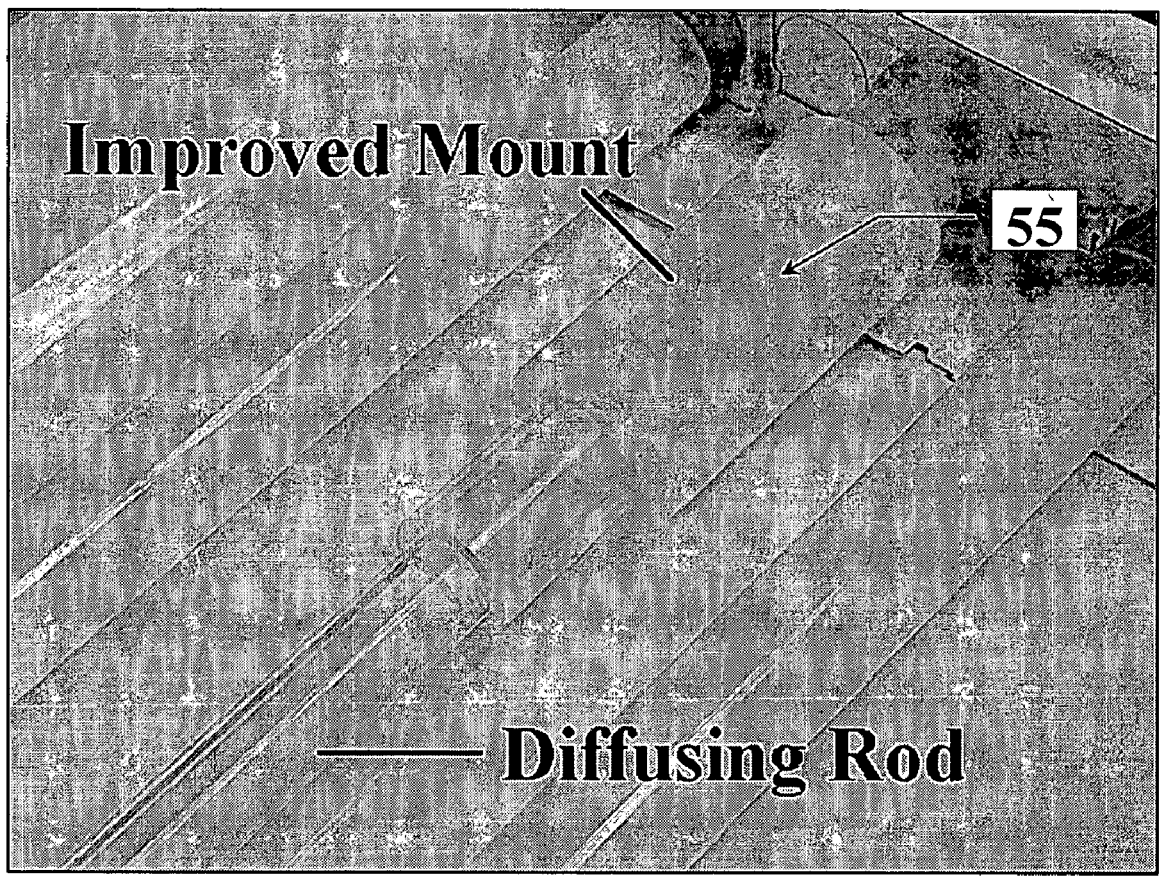
FIG. 11 is a photograph of the improved diffusing rod mount in the hybrid luminaire.
Figure 12:
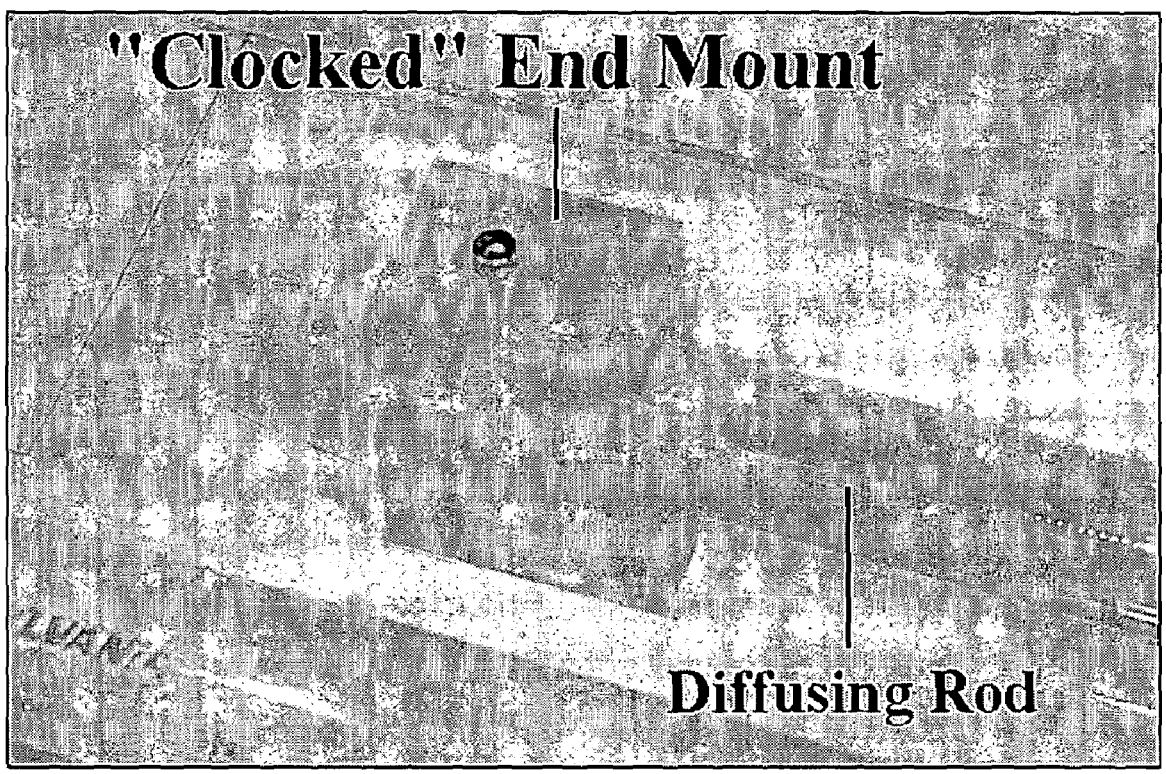
FIG. 12 is a photograph of the "clocked" end mount of the diffusing rod.

Typically, the sunlight exiting the optical fibers produces a conical distribution pattern that is not compatible with the pattern produced by fluorescent lamps. To make the intensity distribution pattern more compatible with that from the fluorescent tubes, it was necessary to transform the light from the fiber into a more cylindrical geometry. Various attempts were tried to construct nonimaging optical components to achieve this goal. Ultimately, the best results were obtained by using a cylindrical, side-emitting diffusing rod 50 developed by 3M and shown in FIG. 10 (3M Side-Emitting Rod Part #: LF180EXN). Two versions of this optic were used in initial tests: the S version, designed for single fiber illumination via one end, and the D version, intended for use with two illuminating fibers. The best linear uniformity of the emitted light was obtained by using the D version with the illuminating fiber at one end of the rod and a reflecting element at the other.

The grooves in the flat surface of the 3M side-emitting rod 50 serve to reflect light out the opposite side of the rod. Ideally, all of the light would be reflected out the side of the rod by the time the last of the rays reached the far end of the rod. In practice, however, a significant portion of the light exits the end of the rod instead of the side. To further improve the efficiency of the side-emitting rod, various reflectors were attached to the end of the rod. Ultimately, a concave spherical mirror (produced by aluminizing the curved side of a plano-convex lens) seemed to produce the best results. The mirror served to reflect and diverge any coaxial light that was not scattered on an initial pass through the rod. The rod was mounted within a custom-machined acrylic holder 55 that allowed a large-core optical fiber to mate with one end of the rod.

In the initial design, two assembled rods were mounted within a four-tube fluorescent fixture. The two side-emitting rods were located on each side of the ballast cover, directly between the two corresponding fluorescent tubes. The side-emitting rods were mounted so that the light was projected toward the acrylic diffuser and out of the fixture. This dual-rod design was selected to provide good spatial distribution match to the light from the fluorescent tubes. Unfortunately, the design required the use of a high-quality splitter (low-loss, 50:50 split) to divide the light from a single fiber into the two light tubes.

The hybrid luminaire was mounted and tested. Instead of using a splitter, two separate optical fibers sources were used. Thus, the measured efficiency did not reflect the additional losses that would be contributed by the connection losses and inherent internal loss associated with using a splitter.

The initial tests of the hybrid luminaire indicated that coupling losses from the fiber to the side-emitting rod were high, leading to reduced efficiency. Design enhancements to the luminaire were added to stabilize the position of the side-emitting rods and improve coupling efficiency. The enhanced version of the dual-rod design was tested to measure the improvement in performance.

To further improve efficiency and lower the cost of the luminaire, the instant invention used only one side-emitting rod 50. By using only one side-emitting rod, the need for a splitter would be obviated, eliminating the connection losses into and out of the splitter as well as the inherent loss within the splitter itself. In addition, the cost of the splitter and the additional side-emitting rod would be eliminated. However, the use of a single side-emitting rod would require two major modifications to the luminaire design. The rod would have to be mounted in the center of the luminaire to maintain symmetry in the intensity distribution pattern, and it would have to be rotated 180° to broaden the intensity distribution pattern.

To enable the side-emitting rod 50 to be centrally mounted, the standard ballast and ballast cover were removed, making the central portion of the luminaire available for development. A compact (16.5-in.×1.25-in.×1-in.), four-bulb, dimmable ballast was obtained from Advance Transformer (Mark 7 IntelliVolt series, product number IZT-4S32) and installed on the rear of the luminaire housing.

A second feature of the invention was necessary to achieve an acceptable intensity distribution pattern from a single emitting rod. To achieve a pattern of sufficient width, the direction of the rod would have to be reversed, directing the light onto the reflective housing 51 of the luminaire and allowing the diffuse reflection to exit the acrylic diffuser, rather than projecting the light directly onto the acrylic diffuser. If the light from the single rod were projected directly onto the acrylic diffuser, the intensity distribution pattern would be unacceptably narrow in comparison to that from the fluorescent lamps. To improve the efficiency and intensity distribution characteristics of the new design, a diffuse reflective film 52 was used in conjunction with the side-emitting rod 50. A "Light Enhancement Film 52" from 3M (Scotchcal 3635-100) was placed on the luminaire housing in the area directly behind the side-emitting rod 50. This film provided a more diffuse reflection and higher reflectivity than the reflective paint in the luminaire (94% vs 90%).

An additional invention feature was added to the single-rod design to further enhance the optical efficiency. Previous designs had used a reflector at the end of the side-emitting rod to direct the coaxial light back through the rod. Though the intention was to force all of the light to eventually be emitted out the side of the rod, some light was suspected of traveling back up the source fiber where it could not be used for illumination. An improvement was made in the single-rod design. Rather than attaching a reflector to the end of the side-emitting rod, a bundle of small optical fibers 53 was attached to the end of the rod and routed back into the central portion of the luminaire. Coaxial light that was not emitted from the side-emitting rod would enter the bundle of fibers and be redirected into the luminaire where it would add to the side-emitted light from the rod. The fibers were simply routed around the ends of the fluorescent tubes and back toward the center of the luminaire where the exiting light was scattered off of the 3M light enhancement film 52. In future embodiments, the fibers could be arranged to achieve a more uniform contribution to the overall intensity distribution.

The light distribution characteristics and overall efficiency for each of the luminaire designs are compared in Table 1.

TABLE 1

Light distribution and efficiency comparisons for each of the luminaire configurations

| Position | Lumens | Percent of total |
|---|---|---|
| Fluorescent lamp system | | |
| End-wall 1 | 1772 | 18 |
| End-wall 2 | 2073 | 21 |
| Side-wall 1 | 1756 | 18 |
| Side-wall 2 | 1661 | 17 |
| Floor | 2438 | 25 |
| Total lumen input 12000 | | |
| Luminaire efficiency 80.8% | | |
| Initial dual-rod luminaire | | |
| End-wall 1 | 319 | 13 |
| End-wall 2 | 511 | 21 |
| Side-wall 1 | 292 | 12 |
| Side-wall 2 | 252 | 10 |
| Floor | 1071 | 44 |
| Total lumen input 4240 | | |
| Luminaire efficiency 57.6% | | |
| Enhanced dual-rod luminaire | | |
| End-wall 1 | 583 | 17 |
| End-wall 2 | 592 | 17 |
| Side-wall 1 | 582 | 17 |
| Side-wall 2 | 507 | 15 |
| Floor | 1203 | 35 |
| Total lumen input 5250 | | |
| Luminaire efficiency 66.0% | | |
| Single-rod luminaire | | |
| End-wall 1 | 456 | 26 |
| End-wall 2 | 338 | 20 |

TABLE 1-continued

Light distribution and efficiency comparisons
for each of the luminaire configurations

| Position | Lumens | Percent of total |
|---|---|---|
| Side-wall 1 | 274 | 16 |
| Side-wall 2 | 264 | 15 |
| Floor | 397 | 23 |
| Total lumen input 2200 | | |
| Luminaire efficiency 78.6% | | |

Note that the actual amount of light used in the comparisons of the fiber optic systems varied considerably. When illuminated by sunlight, the lumen input to the fiber portion of the luminaires is expected to be between 4500 and 5000 lumens. However, the percentage distribution of the light among the walls and floor should not change. The characteristics of the fluorescent lamp system were essentially identical for the three cases and thus are presented only once.

The efficiency of the luminaires shows consistent improvement, with the single-rod luminaire providing almost 79% efficiency. This is very comparable to the 81% efficiency of the fluorescent portion of the luminaire. The light distribution for the single-rod luminaire is comparable to that of the fluorescent system as well, noting that the dual-rod designs placed a higher percentage of the incident light on the floor of the illumination cell. The only undesirable feature of the single-rod luminaire is an uneven distribution of light between the different walls of the illumination cell. In particular, the scattering characteristics of the side-emitting rod in the inverted configuration tended to increase the light on one end-wall of the illumination cell. This is considered to be within the bounds of acceptable variation, but efforts will be made to further equalize the distribution from this design.

A major step toward the realization of using fiber optic transported solar light for internal lighting purposes involves the development of a hybrid luminaire to seamlessly balance lamp and fiber optic transported solar illuminants. Fluctuations in the intensity of collected solar light, due to changing cloud coverage or solar collector movement, requires rapid compensation by electric lamps to maintain a constant room illumination. If the spatial intensity distribution of a hybrid luminaire's electric lamp does not closely match the spatial intensity distribution of the luminaire's fiber optic end-emitted solar illuminant, then the shift between artificial and solar lighting will be noticeable to the occupant and is highly undesirable.

To date, there are a wide variety of commerically-available daylighting sensors manufactured by a variety of vendors. These sensors range in price from $50-$300 and come in a variety of optical packages suitable to various workspace environments (i.e. office spaces, conference rooms, atriums, etc.). Despite the variation in packaging, these sensors all work on essentially the same basic principle. The sensor, which is mounted in the ceiling, contains a plastic lens that images light from the workplane onto a photodetector. The output from the photodetector is a measure of the combined sunlight and artificial lighting levels within a specified viewing angle (also called the sensor's "cone of response")

From the photodetector's output (and the ballast voltage), the sunlight levels versus artificial lighting levels can be calculated. These indirect measurements are used with a control algorithm (either a constant set point or a sliding set point algorithm) to appropriately adjust the intensity of the fluorescent lighting.

When the sunlight and artificial lighting are identically distributed over a given area, current commercial sensors have been shown to perform well. However, when the spatial distribution of the sunlight and artificial lighting are quite different, which is typically the case in an office environment, the indirect calculation of sunlight levels versus artificial lighting levels is inaccurate. Because of the high ratio of uplighting to downlighting associated with sunlight entering through a window, this indirect measurement often results in a sensor that is overly sensitivity to sunlight. As a result, commercially available sensors overcompensate for sunlight, resulting in controlled lighting levels that can fall well below desired workplane illuminance levels.

To improve the performance of daylight harvesting algorithms, a sensor is needed that allows for the independent measurement, as opposed to the combined measurement, of sunlight and artificial light within a controlled area.

Unlike commercial sensors, the daylight harvesting sensor in the instant invention is capable of measuring sunlight and artificial lighting level separately. The daylighting sensor accomplishes this by exploiting the frequency differences between sunlight and fluorescent lighting. Although undetectable to humans, the intensity of fluorescent lighting actually oscillates, or "flickers", at a very high frequency (>10 KHz for most dimmable ballasts). In contrast, sunlight does not flicker and is extremely constant over a short period of time (<1 sec). A high-speed photo-detector is capable of measuring both signals simultaneously as shown in FIG. 8.

The magnitude of the photodetector's high-frequency component is proportional to the fluorescent lighting levels at the workplane. The magnitude of the signal's constant, or DC, component is proportional to the sunlight levels at the workplane.

Figure 8:
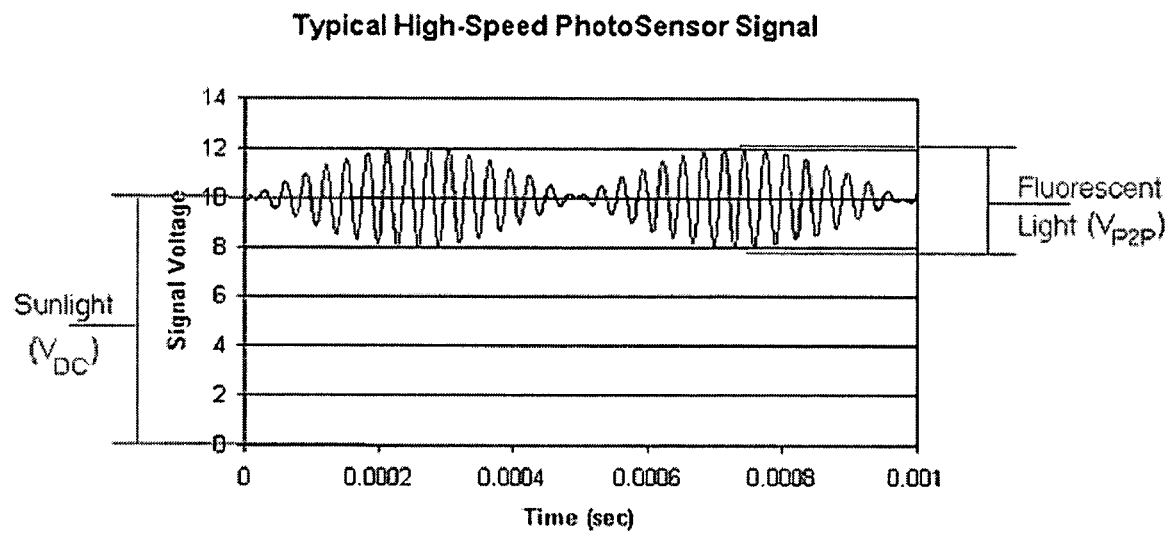
FIG. 8 is a graph showing typical high-speed photosensor signal.

Factoring in phase differences between nearby fluorescent fixtures, which can complicate the simple relationship shown in FIG. 8, the following equation comprises the harvesting sensor's control algorithm:

$$\frac{K_s \cdot V_{DC} + (1-K_s) \cdot m_p \cdot V_{P2P} + (1-K_s) \cdot b_p}{\left[\frac{m_p \cdot V_{P2P} + b_p}{m_B \cdot V_{Ballast} + b_B}\right]} = \text{Constant}$$

where:
$m_p$, $m_B$, $b_p$, $b_B$=are determine during power-up.
$V_{P2P}$=Peak-to-Peak Amplitude of Oscillating Signal
$V_{DC}$=Average DC voltage of signal
$V_{Ballast}$=Voltage to Ballast Control Line
$K_s$=Calibration factor This equation represents the basic control algorithm for workspaces illuminated with sunlight and fluorescent lighting. The ballast voltage (Vballast) is modified to keep the above equation constant with increasing sunlight. Modifications can be made to this control algorithm to accommodate unique lighting environments where sunlight and fluorescent lighting are supplemented with non-fluorescent artificial lighting.

Figure 9:
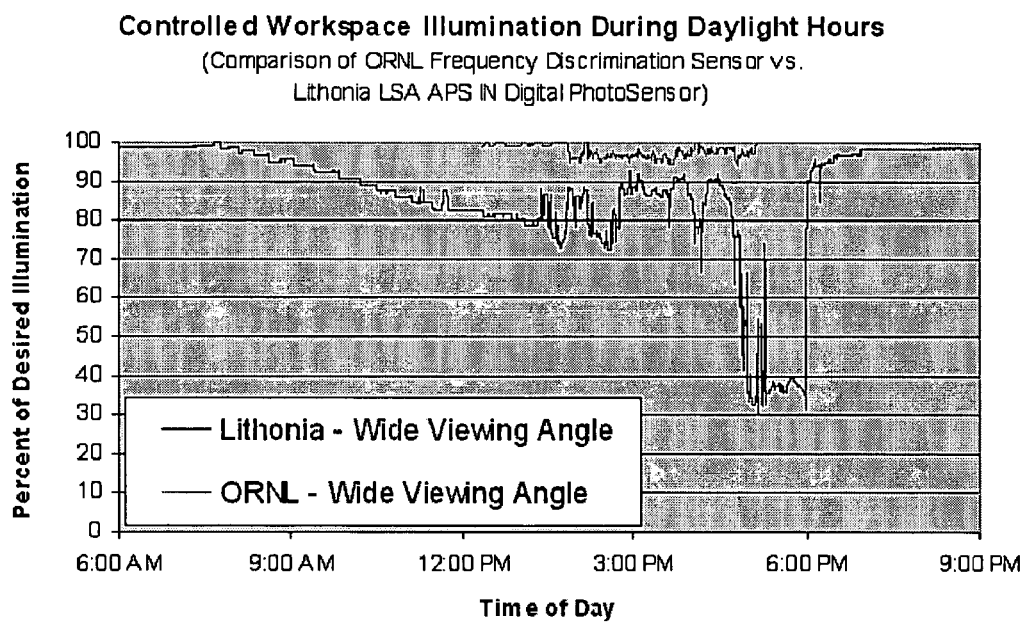
FIG. 9 is a graph of the harvesting daylighting sensor vs. a Lithonia brand sensor.

The performance of a prototype daylight harvesting sensor was tested against leading commercial daylighting sensors. Comparative tests performed in a typical 10'×10' office environment, with a 24"×30" window, demonstrated the sensor's superior performance over commercial sensors. FIG. 9 compares the performance of the harvesting daylighting sensor against a popular daylighting sensor manufactured by Lithonia. In sharp contrast to the commercial sensor, which exhibited large fluctuations in room illumination throughout the day (maximum fluctuation=65%), the harvesting daylighting sensor exhibited only minor illumination fluctuations (maximum fluctuation<5%).

While there has been shown and described what are at present considered the preferred embodiments of the invention, it will be obvious to those skilled in the art that various changes and modifications can be made therein without departing from the scope.

We claim:

1. A hybrid collector comprising;
   a primary mirror for producing reflected full spectrum solar radiation,
   a secondary mirror supported in position for receiving said reflected full spectrum solar radiation and further reflecting said full spectrum radiation onto a fiber receiver, said fiber receiver further comprising;
   a receiver housing,
   a filter removably disposed in said receiver housing,
   a quartz rod removably disposed in said receiver housing,
   a fiber at least partially disposed in said housing and engaged with said quartz rod, said fiber further transmitting said solar radiation to a distribution system.

2. The hybrid collector of claim 1 wherein said secondary mirror is supported by a secondary mount further comprising;
   a non-rigid structure that blocks less than 5% of said reflected full spectrum solar radiation and maintains predetermined optical distances.

3. A fiber receiver comprising;
   a receiver housing,
   a filter removably disposed in said receiver housing,
   a quartz rod removably disposed in said receiver housing,
   a fiber at least partially disposed in said housing and engaged with said quartz rod, said fiber further transmitting light to a light distribution system.

4. A hybrid luminaire comprising;
   a luminaire housing,
   at least one electric light source removably disposed in said luminaire housing,
   at least one fiberoptic light source removably disposed in said luminaire housing, said fiberoptic light source further comprising;
   a cylindrical diffusing rod having an entrance end, exit end, and surface hemisphere with a lower portion and upper portion,
   a polished lower hemisphere,
   a coated upper hemisphere, and
   a coated concave mirror surface disposed on said exit end of said rod.

5. A hybrid luminaire comprising;
   a luminaire housing,
   at least one electric light source removably disposed in said luminaire housing,
   at least one fiberoptic light source removably disposed in said luminaire housing, said fiberoptic light source further comprising;
   a diffuse reflective film attached to said luminaire housing,
   a side-emitting diffusing rod having an entrance end and exit end,
   a large core fiber engaged with said entrance end, and
   at least one optical fiber engaged with said exit end of said diffusing rod, said at least one optical fiber routed back into the central portion of said luminaire housing.

6. A hybrid luminaire comprising;
   a luminaire housing,
   at least one electric light source removably disposed in said luminaire housing,
   at least one fiberoptic light source removably disposed in said luminaire housing,
   at least one photosensor for sensing spatial light intensity, and
   a means for controlling the intensity of the electric light source to a predetermined spatial light intensity constant.

7. A daylight harvesting controller comprising;
   a sensor producing an input signal to said controller, said input signal being proportional to spatial light intensity,
   an integrated circuit producing an output signal, said output signal conditioned to control at least one spatial light emitter to maintain a spatial light intensity constant, wherein said spatial light emitter is a hybrid luminaire.

* * * * *